United States Patent
Wachter et al.

[11] Patent Number: 6,085,742
[45] Date of Patent: *Jul. 11, 2000

[54] INTRAPULMONARY DELIVERY DEVICE

[75] Inventors: Allan Wachter; Stuart Lindsay, both of Tempe, Ariz.

[73] Assignee: Aeromax Technologies, Inc., Phoenix, Ariz.

[*] Notice: This patent is subject to a terminal disclaimer.

[21] Appl. No.: 09/062,033

[22] Filed: Apr. 17, 1998

Related U.S. Application Data

[63] Continuation-in-part of application No. 08/832,369, Apr. 2, 1997, Pat. No. 5,794,612.

[51] Int. Cl.$^7$ .................................................. A61M 11/00
[52] U.S. Cl. ................................ 128/200.23; 128/200.21
[58] Field of Search ..................... 128/200.14, 200.21, 128/203.12, 200.23, 204.23, 204.26

[56] References Cited

U.S. PATENT DOCUMENTS

| | | | |
|---|---|---|---|
| 5,318,016 | 6/1994 | Mecikalski | 128/203.12 |
| 5,507,277 | 4/1996 | Rubsamen et al. | 128/200.14 |
| 5,571,246 | 11/1996 | Alldredge | 128/200.23 |
| 5,794,612 | 8/1998 | Wachter et al. | 128/200.23 |

*Primary Examiner*—Aaron J. Lewis
*Assistant Examiner*—Teena Mitchell
*Attorney, Agent, or Firm*—Nixon Peabody LLP; Daniel W. Sixbey

[57] ABSTRACT

The invention provides an inhalation device for administering a medicament within a prescribed dosage range to avoid over or under administration. The device contains in the mouthpiece or nozzle a channel which follows the Poiseuille equation and provides a flow rate of the fluid containing the medicament at a flow rate of between 0.5 and 3.0 l/s.

11 Claims, 2 Drawing Sheets

INTRAPULMONARY DELIVERY DEVICE

RELATED APPLICATIONS

This application is a continuation-in-part of application Ser. No. 08/832,369 filed Apr. 2, 1997, now U.S. Pat. No. 5,794,612.

FIELD OF THE INVENTION

This invention relates to a structure and method of administering precisely measured doses of a therapeutic by inhalation. More specifically, there is provided an inhalation device which can administer a proper dosage of a medicament by inhalation by providing a controlled flow rate in the mouthpiece of the device.

BACKGROUND OF THE INVENTION

An accurate mechanism for delivering precise drug dose of aerosol drugs into the interior of human beings has been an objective of many workers in the art. One of the most popular aerosol delivery devices is the propellant driven metered dose inhaler (MDI) which releases metered dose of medicine upon each actuation.

U.S. Pat. No. 5,364,838 discloses an intrapulmonary device for administering insulin which contains a system for determining inspirational air flow created by a patient inhaling through the mouthpiece which has a microprocessor that collects data from an airflow detector.

U.S. Pat. No. 5,458,135 discloses a device for administering doses of powder aerosol drugs which contains a microprocessor and a key pad for inputting information to the microprocessor. The device contains a dosage recall button, a LCD which displays dates, times, puffs and dosage history.

None of the prior art devices provide a means for controlling the flow rate so that the inhaled medicament would be within a selected amount to avoid over dosing and/or under dosing.

When the inhalation devices are used by children or invalids, the accuracy of reported doses and/or amount of drug used in the treatment of a pulmonary disease can be questionable. An overdose or an underdose can cause a problem to the patient who is relying upon an accuracy of dosage. A need to know dosage and amount of administered drug is important in preventing underdosing or overdosing.

It is desirable that the patient be able to know if the dose is within the required range. Furthermore, it has been shown that few patients are able to tell when a correct dosage has been administered or if they are properly using the inhalation device.

Workers in the art have attempted to provide a metered dose of a medicant by using dry powder inhalers (DPI). Such devices normally rely on a burst of inspired air that is drawn through the unit. However, these units are disadvantaged in that the force of inspiration varies considerably from person to person. Some patients are unable to generate sufficient flow to activate the unit.

Other workers in the art have refined aqueous nebulization delivery systems. Although such systems require a continuous gas compressor, making them less portable than the MDI's and the DPI's, many nebulizers provide a low velocity aerosol which can be slowly and deeply inhaled into the lungs. Precision of dosage delivery, however, remains a serious problem and it is difficult to determine how much medicament the patient has received. Most nebulizers operate continuously during inhalation and exhalation. Dosage is dependent on the number and duration of each breath. In addition to breath frequency and duration, the flow rate, i.e., the strength of the breath that is taken from a nebulizer can effect the particle size of the dose inhaled. The patient's inhalation acts as a vacuum pump that reduces the pressure in the nebulizer. A strong breath can draw larger unwanted particles of medicant out of the nebulizer. A weak breath, on the other hand, will draw insufficient medicament from the nebulizer.

SUMMARY OF THE INVENTION

According to the present invention, there is provided a device for the administering a dispensable medicament powder or liquid composition for inhalation by a patient which comprise a means for delivering aerosolized doses that includes a nozzle or mouthpiece containing a chamber and a channel which provides a flow rate according to the Poiseuille equation and has a flow rate of about 0.8 to 1.5 l/s, preferably about 1 l/s.

The channel restricts the flow rate of distribution of medicament which provides a pressure chop described by the equation:

$$\Delta P = \frac{v/t_4 \, 8 \, \mu l}{\pi a^4}$$

wherein v/t=F, the flow rate (in $m^3$ per second), $\mu$ is the viscosity of a containing propellant ($1.8 \times 10^{-5}$ $m^{-1}s^{-1}$), l the length of channel and a is the radius of the channel.

The inhalation device can contain a pressured gas for aerosolizing the medicament or rely on the inhalation by the patient to provide the pressure within said device.

It is understood that the pressure amount is intended to mean either an exact pressure amount or a pressure range.

It is an object of the present invention to provide an intrapulmonary delivery device for a prescribed dosage of medicament.

It is a further object of the invention to train a patient to provide a proper inspirational flow rate of medicament.

It is still another object of the invention to provide a system for delivering a precisely measured dosage propelled from an intrapulmonary delivery device.

It is a further object of the invention to provide an inhalation device contains an expansible chamber.

It is a still further object of the invention to provide an inhalation device with a restricted flow rate to prevent excessive flow-rate of medicament.

These and other objects and advantages will be better understood from a reading of the following description of preferred embodiment and the accompanying drawings.

DESCRIPTION OF THE PREFERRED EMBODIMENTS

Figure 1A:
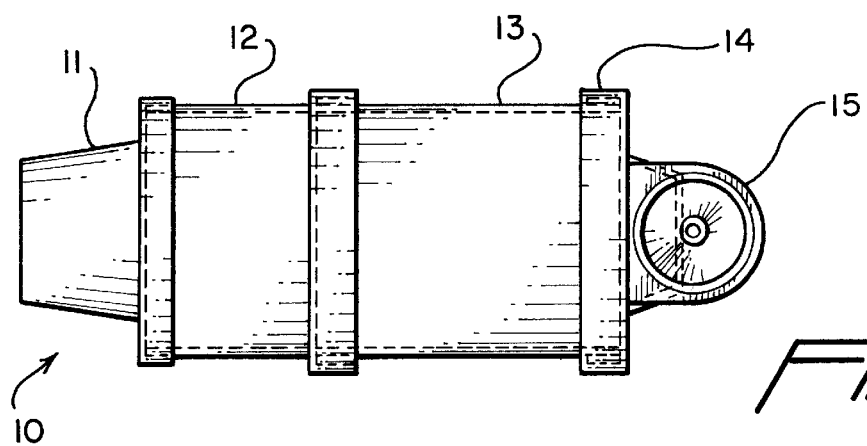
FIG. 1A is a top view of an inhalation device of the invention.
Figure 1B:
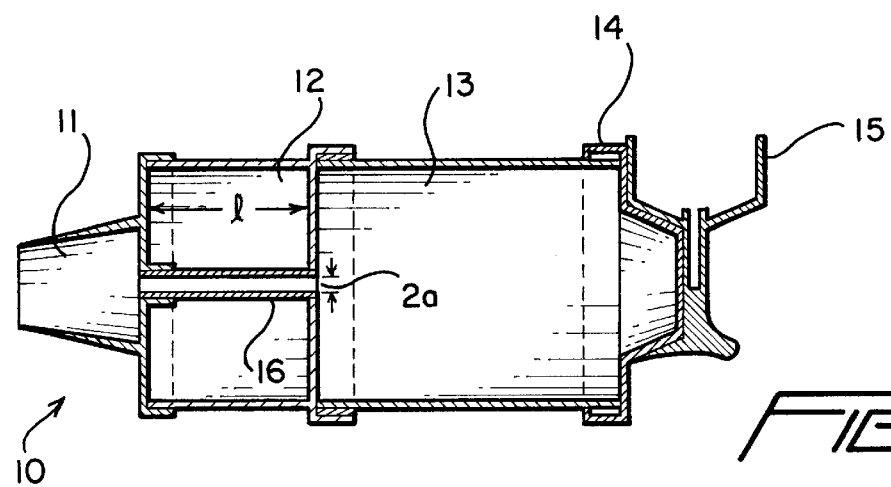
FIG. 1B is a cross-sectional side view of the device of FIG. 1A.

One embodiments of the invention is illustrated in FIGS. 1A and 1B wherein a propellant driven inhalation is shown.

The device 10 comprises a nozzle 11 which is the mouthpiece through which the medicament is delivered. A section 12 which contains the channel 16 is the portion forming a Poiseuille gage type delivery system. Attached to section 12 is the chamber 13 into which a medicament is dispensed from a pressurized container (not shown) which is placed in the activating receptacle 15 of the end part 14. Part 14 can also be of the type which receives a breath actuated medicament container. The conventional nozzles 11 have an opening of about 15 mm and a length of abut 20 mm. The chamber 13 generally has a diameter of about 41 mm.

Figure 2A:
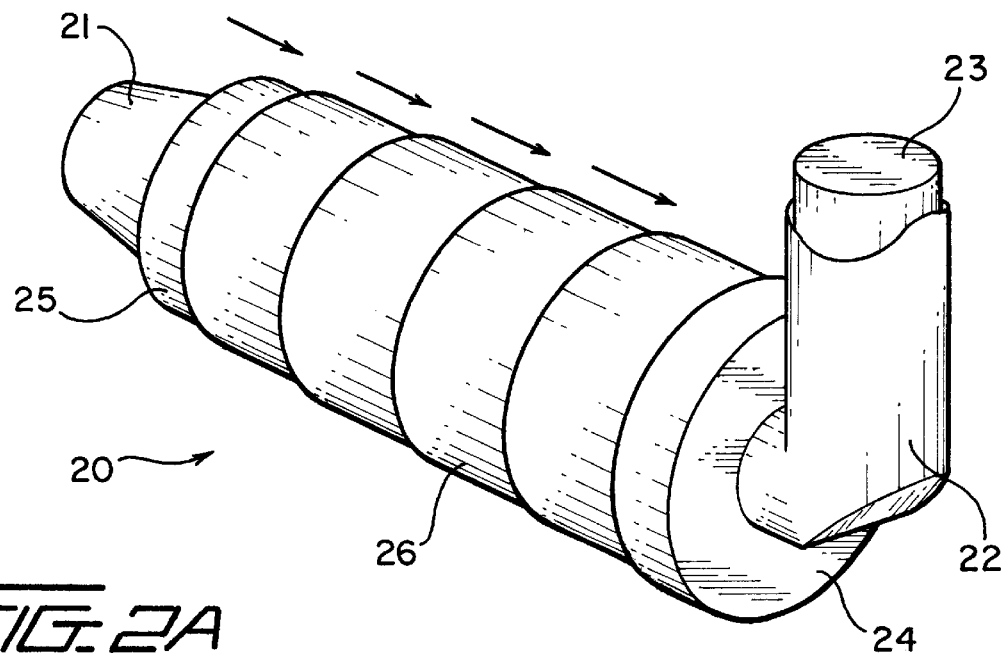
FIG. 2A is a perspective view of a collapsible device according to the present invention.
Figure 2B:
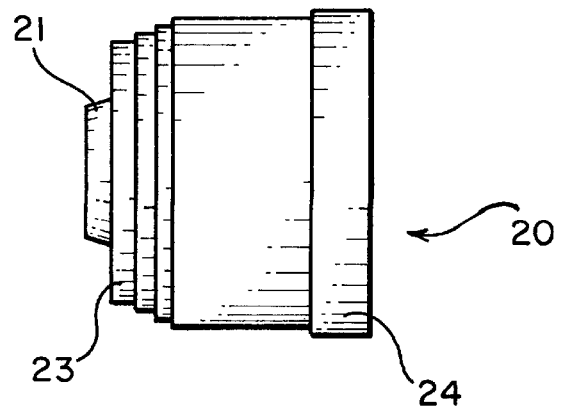
FIG. 2B is a side view of the device of FIG. 2A in a collapsed state.

As shown in FIGS. 2A and 2B, the inhalation device 20 of the invention can contain a collapsible chamber portion 26 which collapses over the part 25 containing the Poiseuille gage mechanism and the mouthpiece 21.

The rear portion 24 of the chamber can be the type to which a gas propelled medicament container 23 and actuator 22 is attached or can have a medicament container attached or forming a part thereof which is actuated by the patient's breath.

The mechanism of a Poiseuille gauge in inhalation channels consists of a channel 16 of diameter $2a$ and length l, through which the aerosol is drawn by inhalation on the mouthpiece. The relatively narrow channel serves to restrict air flow, requiring a relatively large pressure differential to achieve flow rates on the order of a liter per second, the desired optimal inhalation rate for optimal distribution of medication (Ref: Dolovich et al. Chest 80, 911 1981). This limits the tendency of the patient to inhale excessively fast.

The medicament is precisely dispensed because of the low viscosity of air ($1.8 \times 10^{-5}$ m$^{-1}$s$^{-1}$) flow at even hundreds of meters per second is still laminar. Therefore, the pressure drop ($P_2 - P_1 = \Delta P$), wherein $P_1$ is the pressure at the mouthpiece and $P_2$ is ambient pressure, is described by the Poiseuille equation:

$$\Delta P = \frac{v/t_4 \, 8 \, \mu l}{\pi a^4}$$

where $v/t = F$, the flow-rate (in m$^3$ per second), $\mu$ is the velocity of fluid containing the medicament ($1.8 \times 10^{-5}$ m$^{-1}$s$^{-1}$) l the length of the channel and a its radius. The pressure is in units of Pascals, Pa. A channel of 2 mm diameter (a=1 mm) and 3 cm length yields $\Delta P = 10$ kPa for a flow rate of 7.6 l/s ($7.6 \times 10^{-3}$ m$^3$/s). Thus, the desired flow rate of about 0.5 to 3 l/s preferably about 1 l/s.

Figure 3:
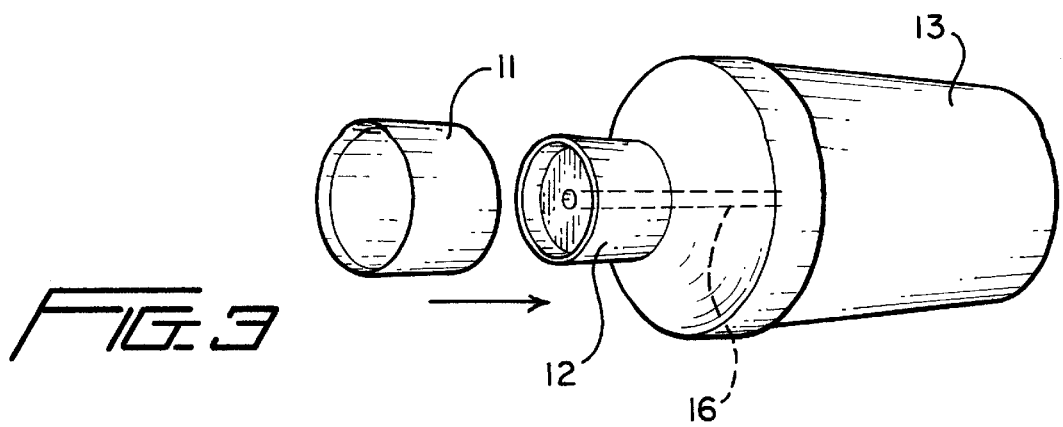
FIG. 3 is an exploded perspective view of a third embodiment of the inhalation device of the present invention.

FIG. 3 shows the device 10 where the channel 16 is formed to extend from within the nozzle or mouthpiece 11 through the section 12 to connect the mouthpiece to the chamber 13. Here the mouthpiece is tubular, as shown in FIG. 2A and fits over one reduced end of the section 12.

The method and device of the present invention are useful for delivering a wide variety of medicaments, drugs, biologically active substances, and the like, to a patient's lung, particularly for systemic delivery of the medicament or the like. The present invention is particularly useful for delivering high value medicaments and drugs, such as proteins and polypeptides, where efficient delivery and amount of drug dosed are of great concern.

According to one embodiment of the invention, the apparatus of the present invention will comprise the following basic components: a means for producing a metered volume of gas, powder, or liquid medicament reservoir that contains the medicament, a holding chamber that efficiently captures the aerosol bolus from either a liquid or a powder, a reservoir that contains the medicament, a holding chamber that efficiently captures the aerosol bolus to maintain the aerosolized particles in suspension and allow a patient to inhale the aerosol by a slow, deep inspiration.

A gas or propellant will usually deliver a preselected volume of gas at greater than about 15 psig in order to produce a sonic velocity jet in an aerosol producing region (although sonic velocity is not always necessary). The pressurized gas is required to efficiently atomize the liquid or break apart the power producing an aerosol having particles that are predominantly 1 to 5 $\mu$m in diameter. In addition, the volume of the gas bolus must be less than a fraction of a patient's inspiratory volume, for example, between 100 to 750 ml. Suitable gas sources include:

1. an air compressor;
2. a compressed gas cylinder;
3. a liquid propellant with a metering valve;
4. a spring piston pump;
5. a pneumatic pump; and
6. sensors for sensing pressure and/or particle density.

The drugs utilized include anti-inflammatory drugs, insulin, analyses, bronchodilaters, proteins, steroids, enzymes, anticholingeric antibiotics and the like.

The present invention is readily adapted for use in existing systems such as PROVENTIL HIA of Key Pharmaceuticals, Inc.

What is claimed is:

1. A delivery device for administering metered doses of medicament from a medicament container for inhalation by a patient comprising:

a mouthpiece having a mouthpiece passage extending therethrough through which medicament can pass, said mouthpiece passage having a first cross sectional size;

a medicament receiving chamber into which medicament from said medicament container is dispensed, a medicament container holder for a medicament container mounted on said medicament receiving chamber, said medicament container holder having an actuator for supplying medicament from a medicament container mounted in said medicament container holder to said medicament receiving chamber; and an elongate, restricted tubular delivery channel connecting the mouthpiece passage with the medicament receiving chamber, said elongate, restricted delivery channel being formed with a length and a second cross sectional size smaller than said first cross sectional size of the mouthpiece passage to restrict and control the flow rate of medicament from the medicament receiving chamber to the mouthpiece passage by requiring the formation of a pressure differential to achieve a flow rate of medicament from the medicament receiving chamber through the elongate restricted delivery channel to the mouthpiece passage.

2. The delivery device of claim 1 wherein said elongate restricted tubular delivery channel is a straight channel which forms a Poiseuille gauge which delivers a flow rate within a range of from 0.5 to 3.0 l/s.

3. The delivery device of claim 1 wherein an enclosed chamber extends between said mouthpiece and said medicament receiving chamber, said enclosed chamber having a first endwall and a second endwall spaced from said first endwall, said mouthpiece extending outwardly from the first endwall with the first endwall extending over said mouthpiece passage, said elongated restricted tubular delivery channel extending through said enclosed chamber and opening at a first end through said first endwall into said mouthpiece passage and opening at a second end through said second endwall into said medicament receiving chamber.

4. The delivery device of claim 3 wherein said elongated restricted tubular delivery channel is a straight channel which forms a Poiseuille gauge.

5. The delivery device of claim 3 wherein said medicament receiving chamber is expandible and collapsible.

6. The delivery device of claim 5 wherein said medicament receiving chamber collapses over said enclosed chamber.

7. The delivery device of claim 1 wherein said elongate restricted tubular delivery channel provides a pressure drop described by the equation:

$$\Delta P = \frac{v/t_4 \, 8 \, \mu l}{\pi a^4}$$

wherein v/t=F, the flow rate (in m³ per second), $\mu$ is the viscosity of a containing propellant ($1.8 \times 10^{-5}$ m$^{-1}$s$^{-1}$), l the length of the restricted delivery channel and a is the radius of the restricted delivery channel.

8. The delivery device of claim 7 wherein an enclosed chamber extends between said mouthpiece and said medicament receiving chamber, said enclosed chamber having a first endwall and a second endwall spaced from said first endwall, said mouthpiece extending outwardly from the first endwall with the first endwall extending over said mouthpiece passage, said elongated restricted tubular delivery channel extending through said enclosed chamber and opening at a first end through said first endwall into said mouthpiece passage and opening at a second end through said second endwall into said medicament receiving chamber.

9. The delivery device of claim 8 wherein said elongate restricted tubular delivery channel is a straight channel which forms a Poiseuille gage which delivers a flow rate within a range of from 0.5 to 3.0 l/s.

10. A delivery device for administering metered doses of propellant driven medicament for inhalation by a patient comprising:

a medicament receiving chamber for receiving metered doses of propellant driven medicament, said medicament receiving chamber being expansible and contractible, a mouthpiece with a mouthpiece channel for passing medicament to a patient, and an elongate delivery tube having a central conduit connecting said mouthpiece channel with said medicament receiving chamber said elongate delivery tube being formed to restrict the flow rate of medicament from the medicament receiving chamber to the mouthpiece and to provide a pressure drop described by the equation:

$$\Delta P = \frac{v/t_4 \, 8 \, \mu l}{\pi a^4}$$

wherein v/t=F, the flow rate (in m³ per second), $\mu$ is the viscosity of a containing propellant ($1.8 \times 10^{-5}$ m$^{-1}$s$^{-1}$), l the length of the central conduit and a is the radius of the central conduit.

11. A delivery device for administering metered doses of medicament from a medicament container for inhalation by a patient comprising:

a mouthpiece;

a medicament receiving chamber into which medicament from said medicament container is dispensed, an enclosed chamber extending between said mouthpiece and said medicament receiving chamber, said mouthpiece being mounted on said enclosed chamber, and a straight, elongate, restricted, tubular delivery channel received within said mouthpiece and extending from within said mouthpiece through said enclosed chamber to said medicament receiving chamber to provide medicament from said medicament receiving chamber to said mouthpiece, said straight, elongate, restricted tubular delivery channel being formed to restrict and control the flow rate of medicament from the medicament receiving chamber through the mouthpiece by requiring the formation of a pressure differential to achieve such flow rate, the straight, elongate, restricted, tubular delivery channel forming a Poiseuille gauge which delivers a flow rate of from 0.5 to 3.0 l/s.

* * * * *